(12) United States Patent
Slager (10) Patent No.: US 10,098,846 B2
(45) Date of Patent: Oct. 16, 2018

(54) DRUG-CONTAINING PARTICULATE COMPOSITION WITH CATIONIC AGENT, ASSOCIATED MEDICAL DEVICES, AND METHODS FOR TREATMENT

(71) Applicant: Surmodics, Inc., Eden Prairie, MN (US)

(72) Inventor: Joram Slager, Saint Louis Park, MN (US)

(73) Assignee: SURMODICS, INC., Eden Prairie, MN (US)

( * ) Notice: Subject to any disclaimer, the term of this patent is extended or adjusted under 35 U.S.C. 154(b) by 0 days.

(21) Appl. No.: 15/474,487

(22) Filed: Mar. 30, 2017

(65) Prior Publication Data

US 2017/0281557 A1 Oct. 5, 2017

Related U.S. Application Data

(60) Provisional application No. 62/315,917, filed on Mar. 31, 2016.

(51) Int. Cl.

| | |
|---|---|
| *A61K 9/50* | (2006.01) |
| *A61K 47/34* | (2017.01) |
| *A61K 47/22* | (2006.01) |
| *A61K 31/365* | (2006.01) |
| *A61M 25/10* | (2013.01) |

(52) U.S. Cl.
CPC .......... *A61K 9/5026* (2013.01); *A61K 9/5031* (2013.01); *A61K 9/5073* (2013.01); *A61K 9/5089* (2013.01); *A61K 31/365* (2013.01); *A61K 47/22* (2013.01); *A61K 47/34* (2013.01); *A61M 25/104* (2013.01); *A61M 2025/105* (2013.01)

(58) Field of Classification Search
CPC ...... A61K 9/50; A61K 9/5031; A61K 9/5073; A61K 31/365; A61K 47/22; A61K 47/34
See application file for complete search history.

(56) References Cited

U.S. PATENT DOCUMENTS 5,312,863 A * 5/1994 Van Rheenen .......... C09D 7/45
524/555
7,232,486 B2 6/2007 Keri et al.
(Continued)

FOREIGN PATENT DOCUMENTS

WO 2008/013416 A1 1/2008
WO 2008/014222 A1 1/2008
(Continued)

OTHER PUBLICATIONS

Love, K.T. et al. (2010) "Lipid-like Materials for Low-Dose, in Vivo Gene Silencing", PNAS 107:1864-1869.
(Continued)

*Primary Examiner* — Carlos A Azpuru
(74) *Attorney, Agent, or Firm* — Kagan Binder, PLLC (57) ABSTRACT

The disclosure provides bioactive agent-containing particulates that include bioactive agent, biocompatible polymer, negatively charged groups, and a cationic agent. The particulates can be associated with a medical device, such as a balloon catheter, which can be used to move the particulates to a treatment site. Transfer of the particulates from the device to tissue is facilitated by the arrangement of the cationic and bioactive agent-containing particulates.

20 Claims, 2 Drawing Sheets

(56) References Cited

U.S. PATENT DOCUMENTS

| | | |
|---|---|---|
| 7,842,312 B2 | 11/2010 | Burgermeister et al. |
| 8,048,448 B2 | 11/2011 | Ludwig et al. |
| 8,337,733 B2 | 12/2012 | Westedt et al. |
| 8,585,642 B2 | 11/2013 | Doshi et al. |
| 8,668,667 B2 | 3/2014 | Chappa |
| 8,927,000 B2 | 1/2015 | Chappa et al. |
| 8,951,545 B2 | 2/2015 | Arps et al. |
| 2005/0037050 A1 | 2/2005 | Weber |
| 2006/0169199 A1 | 8/2006 | Keri et al. |
| 2007/0128731 A1 | 6/2007 | Deshmukh et al. |
| 2008/0085880 A1 | 4/2008 | Viswanath et al. |
| 2008/0213375 A1 | 9/2008 | Ray et al. |
| 2009/0246252 A1 | 10/2009 | Arps et al. |
| 2012/0004605 A1 | 1/2012 | Chappa |
| 2012/0028908 A1 | 2/2012 | Viswanath et al. |
| 2012/0083733 A1 | 4/2012 | Chappa |
| 2012/0165786 A1 | 6/2012 | Chappa et al. |
| 2012/0177741 A1* | 7/2012 | Moslemy ............ A61K 9/0048 424/489 |
| 2013/0035483 A1 | 2/2013 | Zeng et al. |
| 2014/0336571 A1 | 11/2014 | Slager et al. |
| 2015/0017219 A1 | 1/2015 | Slager et al. |

FOREIGN PATENT DOCUMENTS

| | | | |
|---|---|---|---|
| WO | 20111123730 A1 * | 3/2011 | ............... A61K 9/50 |
| WO | 2012/026896 A1 | 3/2012 | |
| WO | 2012/101455 A1 | 8/2012 | |

OTHER PUBLICATIONS

Hornedo, N.R. et al. (1999) "Significance of Controlling Crystallization Mechanisms and Kinetics in Pharmaceutical Systems", Pharmaceutical Sciences 88:651-660.

Murdock, R.C. et al. (2008) "Characterization of Nanomaterial Dispersion in Solution Prior to In Vitro Exposure Using Dynamic Light Scattering Technique", Toxicological Sciences 101:239-253.

Wen et al. (2007), "Effects of Polyethylenimine on the Dispersibility of Hollow Silica Nanoparticles", Front. Chem. Eng. China 1:277-282.

Kohler, U., et al. (2008) "Investigations on non-Spherical Reference Material Using Laser Diffraction and Dynamic Image Analysis", Particulate Systems Analysis, 1-5.

https://www.sympatec.com/EN/ImageAnalysis/Fundamentals.html, "Fundamentals—Particle Size and Shape Calculation by Image Analysis", Sympatec GmbH System-Partikel-Technik; retrieved Jan. 6, 2016.

* cited by examiner

Fig. 1

DRUG-CONTAINING PARTICULATE COMPOSITION WITH CATIONIC AGENT, ASSOCIATED MEDICAL DEVICES, AND METHODS FOR TREATMENT

CROSS-REFERENCE TO RELATED APPLICATION

The present non-provisional application claims the benefit of commonly owned provisional Application have Ser. No. 62/315,917, filed on Mar. 31, 2016, entitled DRUG-CONTAINING PARTICULATE COMPOSITION WITH CATIONIC AGENT, ASSOCIATED MEDICAL DEVICES, AND METHODS FOR TREATMENT, which Application is incorporated herein by reference in its entirety.

FIELD OF THE INVENTION

The present invention relates to the field of drug delivery using drug particles and medical devices.

BACKGROUND OF THE INVENTION

The release of drugs from an implanted medical device has been shown to be beneficial for the function of devices and the treatment of various medical conditions. For example, delivery of a drug from the device surface can prevent cellular responses initiated by the presence of the implantable device. Also, drug released from the device can prevent conditions that would otherwise shorten the functional life of the device following implantation. Drug released from the device may also be directed at treating a diseased area of the body such at a target tissue.

However, the transfer of drugs from a medical device to a target tissue can be challenging. For example, in some systems elution of a drug from a polymer matrix may not be sufficient to provide a therapeutic amount of the drug to the target tissue. In some systems drug may be released at or move to a site other than the target tissue. Further, many of the drug delivery coating are made for devices with "static surfaces", that is, surfaces that do not increase in area. Typically, polymer systems that form durable coatings are suitable for these static surfaces. However, on surfaces that are non-static (e.g., elastic surfaces) such durable coatings may not always be appropriate.

SUMMARY OF THE INVENTION

The invention generally bioactive agent delivery composition that includes bioactive agent-containing particulates associated with a cationic agent. The composition can be associated with an implantable or insertable medical device which can be used to move the particulate composition to a treatment site. In studies associated with the current invention, it has been found transfer of the particulates to tissue is facilitated by the arrangement of the cationic and bioactive agent-containing particulates.

In one embodiment the invention provides a bioactive agent delivery composition comprising bioactive agent-containing particulates. In one arrangement, the bioactive agent-containing particulates include a core particle comprising bioactive agent and a first biocompatible polymer; and a layer around the core particle comprising a second biocompatible polymer and that comprises negatively charged groups, wherein the second biocompatible polymer is more water soluble than the first biocompatible polymer. A cationic agent is associated with the negatively charged groups of the particulate and provides the particulate with a positive zeta-potential.

The first biocompatible polymer can be a degradable organic solvent soluble polymer, such as an aliphatic polyester block copolymer. The bioactive agent can be one that provides antirestenotic effects, such as antiproliferative, anti-platelet, and/or antithrombotic effects, such as a member of the macrolide (e.g., rapamycin) or taxane (paclitaxel) drug family. The second biocompatible polymer can be an acid group-containing polymer, such as an acrylic acid polymer. The cationic agent can also be a biocompatible polymer, such as polyethyleneimine.

In embodiments, the particle composition is associated with a medical device. Using a transiently insertable medical device the particle composition can be transferred from the device to a target tissue for treatment of a condition. Embodiments of the invention include the particle composition associated with a balloon catheter. For example, the particle composition can be associated with a hydrogel coating on an expandable (e.g., balloon) surface. Upon expansion of the balloon the particulates are placed in contact with a target tissue, and the cationic agent facilitates the bulk transfer of particulates to the tissue.

Accordingly, the invention provides a method for treating a subject which includes placing a bioactive agent delivery composition of the disclosure, or a medical device according bioactive agent delivery composition, wherein the bioactive agent is released from the particulates and treats a condition in the subject. Release of bioactive agent from the particulates may include degradation of the first biocompatible polymer.

In another embodiment, the invention also provides methods for forming a bioactive agent delivery composition comprising a bioactive agent-containing particulate. The method includes forming a particle comprising a core particle comprising bioactive agent and a first biocompatible polymer, and a second biocompatible polymer comprising negatively charged groups, that is more water soluble first biocompatible polymer. The particle is then contacted with a composition comprising cationic agent to associate cationic agent with the particulates.

In an exemplary method the particulate can be formed by providing a first composition comprising the bioactive agent and the first biocompatible polymer, and adding the first composition to a second composition comprising the second biocompatible polymer to form a mixture, emulsifying the mixture, and adding the emulsified mixture to an aqueous composition to form the particulates.

DETAILED DESCRIPTION

The embodiments of the present disclosure described herein are not intended to be exhaustive or to limit the disclosure to the precise forms disclosed in the following detailed description. Rather, the embodiments are chosen and described so that others skilled in the art can appreciate and understand the principles and practices of the present disclosure.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the present disclosure provides bioactive agent delivery composition that includes drug-containing particulates, methods for forming these particulates, and medical devices having associated composition with particulates. The particulates are formed by preparing a drug-containing particle (e.g., a core particle) along with biocompatible polymer that has negatively charged groups or that can be treated to provide negatively charged groups, and then associating a cationic agent with the negatively charged groups of the particulate to provide the particulate with a positive zeta-potential.

In a treatment method, the bioactive agent-containing particulates can be placed in a subject, alone or in association with a delivery article or composition, in a manner so the bioactive agent becomes therapeutically available to the subject. In more specific delivery approaches, the bioactive agent-containing particulates are associated with an implantable delivery article for the site-specific release of the bioactive agent.

The term "bioactive agent," (which can also be referred to as a drug, a therapeutic agent, therapeutic compound, pharmaceutical, or the like) refers to an inorganic or organic molecule, which can be synthetic or natural, that causes a biological effect when administered in vivo to an animal, including but not limited to birds and mammals, including humans. A partial list of bioactive agents is provided below. One may choose any one of the bioactive agents to be included in the particulates, or in combination with any other bioactive agent. A comprehensive listing of bioactive agents can be found in The Merck Index, Thirteenth Edition, Merck & Co. (2001).

Bioactive agents may optionally be described with regards to one or more properties such as size (molecular weight), solubility in a solvent, pharmacokinetic properties, etc.

Particulates of the disclosure can include bioactive agents falling within one or more of the following drug classes: ACE inhibitors, actin inhibitors, analgesics, anesthetics, anti-hypertensives, anti polymerases, antisecretory agents, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, prostaglandins, remodeling inhibitors, statins, steroids, thrombolytic agents, tranquilizers, vasodilators, and vasospasm inhibitors.

The bioactive agent can provide antirestenotic effects, such as antiproliferative, anti-platelet, and/or antithrombotic effects. The bioactive agent that provides such an effect can be a member of the macrolide or taxane drug family.

Macrolides are characterized by a large macrocyclic lactone ring, which can be optionally defined by the number of atoms in the ring. The macrocyclic ring includes at least 7 ring atoms selected from carbon, nitrogen, oxygen, sulfur, silicon, phosphorous. Ring atom(s) can optionally be substituted with oxygen, and contain one or more degrees of unsaturation (double or triple bonds). Macrolide compounds of the disclosure can include those that are multicyclic, such as bi- or tricyclic. Some macrolides include sugar molecules (e.g., two or more) bonded to the macrocyclic ring. Many macrolides are found as natural products and belong to the polyketide class of secondary metabolites from various prokaryotic and eukaryotic organisms. Many macrolide therapeutics are chemically synthesized derivatives of naturally-occurring macrolides. Use of non-antibiotic macrolides can be desirable for various indications, such as to prevent or minimize tissue response associated with inflammation, fibrosis, and thrombosis.

Non-antibiotic macrolides include rapamycin (e.g., sirolimus, Rapamune™) everolimus (e.g., Zortress™), pimecrolimus, temsirolimus, fujimycin/tacrolimus, deforolimus, zotarolimus, and biolimus. Chemical structures of these non-antibiotic macrolides are known in the art.

Many of the non-antibiotic macrolides, such as rapamycin, have desirable immunosuppressive and antiproliferative properties. Rapamycin can inhibit growth factor- and mitogen-induced proliferation of T lymphocytes when the rapamycin-FKBP12 complex binds to an effector, and arrests the G1 to S transition of the cell cycle.

Taxanes are diterpenes that are chemically defined by a taxadiene core. Exemplary taxanes include paclitaxel, (Taxol), docetaxel (Taxotere), and cabazitaxel, which can be used as chemotherapy agents. Taxanes generally have poor solubility in water.

The bioactive agent can be a steroid. Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

The bioactive agent can be a statin. Examples of statins include lovastatin, pravastatin, simvastatin, fluvastatin, atorvastatin, cerivastatin, rosuvastatin, and superstatin.

The bioactive agent can be an antithrombotic. Representative examples of bioactive agents having antithrombotic effects include heparin, heparin derivatives, sodium heparin, low molecular weight heparin, hirudin, lysine, prostaglandins, argatroban, forskolin, vapiprost, prostacyclin and prostacyclin analogs, D-phe-pro-arg-chloromethylketone (synthetic antithrombin), dipyridamole, glycoprotein Iib/IIIa platelet membrane receptor antibody, coprotein Iib/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The bioactive agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifibatide (Integrilin™) or tirofiban (Agrastat™).

The bioactive agent can be an immunosuppressive agent, for example, cyclosporine, CD-34 antibody, or mycophenolic acid.

The bioactive agent can be a cell response modifier. Cell response modifiers include chemotactic factors such as platelet-derived growth factor (pDGF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin.

The bioactive agent can be a surface adhesion molecule or cell-cell adhesion molecule. Exemplary cell adhesion molecules or attachment proteins, such as extracellular matrix proteins, include fibronectin, laminin, collagen, elastin, vitronectin, tenascin, fibrinogen, thrombospondin, osteopontin, von Willibrand Factor, bone sialoprotein (and active domains thereof), and hydrophilic polymers such as hyaluronic acid, chitosan and methyl cellulose, and other proteins, carbohydrates, and fatty acids. Other cell-cell adhesion molecules include N-cadherin and P-cadherin and active domains thereof.

For purposes of explaining aspects of the disclosure, an exemplary bioactive agent that can be included in the particulates is rapamycin. Rapamycin has a molecular weight of 914.17 and molecular formula: $C_{51}H_{79}NO_{13}$. It is insoluble in water, but soluble in ethanol (2 mM), methanol (25 mg/mL), DMSO (25 mg/mL), chloroform, (5 mg/mL), ether, acetone and N,N-dimethylformamide. As commercially supplied, rapamycin exists as one isomer (structurally homogeneous) in the solid form as indicated by X-rays whereas in solution there are two conformational isomers (approx. 4:1) which exist in equilibrium.

Rapamycin is commercially available as a manufacturer's preparation in powdered form (e.g., a "stock composition"). Observed using magnification, the powder can be in the form of flakes having irregular shapes (e.g., jagged outer surfaces) and of various sizes. The sizes of the flakes is rather large, having minimal dimensions of generally greater than about 25 µM, and more typically greater than about 100 µM. Stock compositions of rapamycin in powdered form are commercially available from various sources, such as LC Laboratories (Woburn, Mass.) and Sigma Aldrich. Other non-antibiotic macrolides, antibiotic macrolides, and ketolides, are commercially available, or can be prepared using techniques known in the art.

The macrolide compound, such as rapamycin, can optionally be subjected to any purification or enrichment process prior to being used to form the particulates of the disclosure. Exemplary optional purification or enrichment techniques include one or more affinity, hydrophobic, size exclusion, centrifugal, and liquid chromatographies (such as HPLC).

In one aspect (e.g., a first particle aspect of the disclosure), the bioactive agent particulates include a core particle having a bioactive agent and a first biocompatible polymer. There is a layer around the core particle that includes a second biocompatible polymer which includes negatively charged groups. The second biocompatible polymer is chosen to be more water soluble than the first biocompatible polymer. A cationic agent is associated with the negatively charged groups on the particulate in a manner that provides the particulate with and overall positive zeta-potential. "Biocompatible" polymers are those that do not provoke any significant adverse effects when introduced into the body.

In a mode of practice, the particles of the disclosure can be prepared by first preparing a first composition that includes the bioactive agent and first biocompatible polymer. Next, the first composition is contacted with a composition that includes the second biocompatible polymer having negatively charged groups. This forms an intermediate particle with negatively charged groups on the outer surface, and a core particle including the bioactive agent and first biocompatible polymer. Next, the intermediate particle is contacted with a composition that include cationic agent so that the resulting particulate has a positive zeta-potential.

Solubility terms can be used to describe components of the particulates, including bioactive agents, polymers, cationic agent, as well as other optional components. Solubility refers to the level to which a solute (e.g., bioactive agents, polymers, cationic agent) dissolves in a solvent. For a solute in a particular solvent, "practically insoluble", or "insoluble" refers to having a solubility of 1 part moiety per more than 10,000 parts of solvent, "very slightly soluble" refers to having a solubility of from 1 part moiety per 1000 to 10,000 parts of solvent; "slightly soluble" refers to having a solubility of 1 part moiety per from 100 to 1000 parts of solvent; "sparingly soluble" refers to having a solubility of 1 part moiety from 30 to 100 parts of solvent; "soluble" refers to having a solubility of at least 1 part moiety per from 10 to 30 parts solvent, "freely soluble" refers to having a solubility of at least 1 part moiety per from 1 to 10 parts solvent, or "very soluble" refers to having a solubility of greater than 1 part moiety per from 1 part solvent, as measured at about room temperature. These descriptive terms for solubility are standard terms used in the art (see, for example, *Remington: The Science and Practice of Pharmacy*, 20th ed. (2000), Lippincott Williams & Wilkins, Baltimore Md.). The solubility, or lack thereof, of bioactive agents, polymers, and cationic agents can be described in any desired coating solvent, such as water or an organic solvent. Solubility of a solute can be obtained from the literature or readily determined by one of skill in the art.

In aspects, the first biocompatible polymer can have a water solubility that is less that the solubility of the second biocompatible polymer in water. For example, the first biocompatible polymer can be insoluble or very slightly soluble in water. The second polymer can have a water solubility that is at least about 10 times, at least about 20 times, at least about 30 times, at least about 40 times, or at least about 50 times greater than the solubility of the first polymer in water. Conversely, the first biocompatible polymer can be defined with regards to its solubility in an organic solvent, wherein the first biocompatible polymer is soluble, freely soluble, or very soluble in the organic solvent. For example, the first polymer can have a solubility that is at least about 10 times at least about 20 times, at least about 30 times, at least about 40 times, or at least about 50 times greater than the solubility of the second polymer in an organic solvent.

The first biocompatible polymer can be an organic solvent-soluble degradable polymer. Examples of degradable polymers can include those with hydrolytically unstable linkages in the polymeric backbone. The degradable polymers can exhibit bulk erosion or surface erosion characteristics. Synthetic degradable polymers can include: degradable polyesters (such as poly(glycolic acid), poly(lactic acid), poly(lactic-co-glycolic acid), poly(dioxanone), polylactones (e.g., poly(caprolactone)), poly(3-hydroxybutyrate), poly(3-hydroxyvalerate), poly(valerolactone), poly(tartronic acid), poly(β-malonic acid), poly(propylene fumarate)); degradable polyesteramides; degradable polyanhydrides (such as poly(sebacic acid), poly(1,6-bis(carboxyphenoxy)hexane, poly(1,3-bis(carboxyphenoxy)propane); degradable polycarbonates (such as tyrosine-based polycarbonates); degradable polyiminocarbonates; degradable polyarylates (such as tyrosine-based polyarylates); degradable polyorthoesters; degradable polyurethanes; degradable polyphosphazenes; and degradable polyhydroxyalkanoates; and copolymers thereof.

In some aspects the first polymer is a biodegradable block copolymer comprising hydrophilic and hydrophobic blocks. The linkages between the blocks can be biodegradable or biostable, and the hydrophilic and hydrophobic blocks can be either or both biodegradable or biostable, with at least one portion of the copolymer being biodegradable.

In some aspects the hydrophobic blocks include a biodegradable polymeric segment selected from polycaprolactone (PCL), polyvalerolactone (PVL), poly(lactide-co-glycolide) (PLGA), polylactic acid (PLA), polybutyrolactone (PBL), polyglycolide, polypropiolactone (PPL), and polytrimethylene carbonate.

Exemplary hydrophilic blocks can be selected from polymer segments formed from monomers such as ethylene glycol, ethylene oxide, vinyl alcohol, propylene oxide, vinyl pyrrolidone, hydroxy ethyl methacrylate, and hydroxy ethyl acrylate.

Exemplary hydrophilic blocks include (PEO), polyvinyl alcohol (PVA), poly(vinyl pyrrolidone) (PVP), polyacrylamide, poly(hydroxy alkyl methacrylate), poly(hydroxy ethyl methacrylate), hydrophilic polyurethane, HYPAN, oriented HYPAN, poly(hydroxy ethyl acrylate), poly(ethyloxazoline), and polyamines (e.g., Jeffamine™).

In some aspects the second polymer comprises a polyalkoxyalkane block. Representative examples of polyalkoxyalkane blocks include poly(ethylene glycol), tetraethylene glycol, triethylene glycol, trimethylolpropane ethoxylate, and pentaeerythritol etholxylate blocks.

Exemplary hydrophilic blocks have a molecular weight of about 100 Da to about 5000 Da, or about 250 Da to about 3500.

In some aspects, the degradable polymers include at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous and has one or more glass transition temperatures (TO of at most 37° C. (Tg) at physiological (body) conditions. The pre-polymers A and B can be a hydrolysable polyester, polyetherester, polycarbonate, poly estercarbonate, poly-anhydride or copolymers thereof, derived from cyclic monomers such as lactide (L,D or L/D), glycolide, ε-caprolactone δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). The composition of the pre-polymers may be chosen in such a way that the maximum glass transition temperature of the resulting copolymer is below 37° C. at body conditions. To fulfill the requirement of a Tg below 37° C., some of the above-mentioned monomers or combinations of monomers may be more preferred than others. This may by itself lower the Tg, or the pre-polymer is modified with a polyethylene glycol with sufficient molecular weight to lower the glass transition temperature of the copolymer. The degradable multi-block copolymers can include hydrolysable sequences being amorphous and the segments may be linked by a multifunctional chain-extender, the segments having different physical and degradation characteristics. For example, a multi-block co-polyester consisting of a glycolide-ε-caprolactone segment and a lactide-glycolide segment can be composed of two different polyester pre-polymers. By controlling the segment monomer composition, segment ratio and length, a variety of polymers with properties that can easily be tuned can be obtained. Such degradable multi-block copolymers can specifically include those described in U.S. Publ. App. No, 2007/0155906, the content of which is herein incorporated by reference in its entirety.

Specific examples of these types of degradable copolymers include poly(ether ester) multiblock copolymers based on poly(ethylene glycol) (PEG) and poly(butylene terephthalate) (PBT) that can be described by the following general structure:

where —$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. In embodiments, n can be selected such that the molecular weight of the PEG block is between about 300 and about 4000. X and y can be selected so that the multiblock copolymer contains from about 55% up to about 80% PEG by weight. The properties of copolymer can be changed by varying the values of n, x and y in the copolymer structure. An exemplary copolymer of this class is $PEG_{1000}$-45PBT-55 which is a copolymer of a poly(butyleneterephthalate-co-ethylene glycol) copolymer with 45% (wt) polyethylene glycol having an average molecular weight of 1000 kD and 55% (wt) butyleneterephthalate. $PEG_{1000}$-45PBT-55 is commercially available from OctoPlus (Leiden, Netherlands) under the product name PolyActive™.

Another example of these types of degradable copolymers include poly(ether ester) multiblock copolymers based on poly(ethylene glycol) (PEG) and one or more of glycolide, lactide, and/or caprolactone monomers or polymer segments. As specific example is 20GAPEGCL-80GALA, which is a block copolymer of 20% (wt) glycolide-polyethylene glycol-caprolactone "GAPEGCL" and 80% (wt) glycolide-lactide "GALA".

An initial step in the process of preparing the first particle aspect of the disclosure involves preparing a liquid composition including the bioactive agent and the first degradable biocompatible polymer. A solvent or solvent mixture can be chosen to dissolve both the bioactive agent and the first degradable biocompatible polymer.

Exemplary solvents or dispersant include, but are not limited to, aromatic hydrocarbons, such as benzene, xylene (e.g., ortho-xylene, para-xylene, or meta-xylene) and toluene; C1-C4 alcohols such as methanol, ethanol (EtOH), isopropanol (IPA), n-butanol, isobutyl alcohol and t-butyl alcohol; halogenated organic solvents such as dicholoroethane (DCE), dichloromethane (DCM), chloroform, and ethyl trifluroacetate (ETFA); ketones such as methyl isobutyl ketone (MIBK), 3-pentanone (diethyl ketone) acetone, 2-butanone (MEK); acetonitrile (ACN); ethers such as isopropyl ether (IPE) and tetrahydrofuran (THF); aliphatic hydrocarbons such as hexane, heptane, or the like; and esters such as ethyl acetate and butyl acetate.

The bioactive agent and first degradable biocompatible polymer can be dissolved in the liquid composition at a desired concentration and ratio. With regards to concentration, in embodiments, the bioactive agent and first degradable biocompatible polymer can be dissolved in a total amount in the range of about 50 mg/mL to about 1 g/mL, about 150 mg/mL to about 600 mg/mL, or about 250 mg/mL to about 350 mg/mL. A total exemplary concentration is about 300 mg/mL. With regards to concentration, in embodiments, the bioactive agent and first degradable biocompatible polymer can be present in the composition at a weight ratio in the range of about 1:20 to about 2:1, about 1:10 to about 1:1, about 1:5 to about 1:1.5, or about 1:3 to about 1:1.2, respectively. An exemplary ratio is about 1:2, respectively.

The bioactive agent and first degradable biocompatible polymer can be mixed in the solvent at any temperature so the components can dissolve in a desired period of time. The composition can be agitated, such as stirred, either manually or mechanically, to increase the rate of dissolution.

Optionally, one or more other components can be included in the solvent along with the bioactive agent and first degradable biocompatible polymer. One type of component is an alkyl-substituted chromanol. Exemplary alkyl-substituted chromanols are of Formula I:

wherein $R^1$, $R^2$, $R^3$, and $R^4$ are independently selected from the group consisting of methyl (—CH$_3$) and hydrogen (—H); $R^5$ is a saturated or partially saturated, linear or branched C4-C16 alkyl group; $R^6$ is selected from the group consisting of H, —C(O)R$^7$, wherein $R^7$ is C1-C6 alkyl, and —R$^8$(CH$_2$CH$_2$O)$_n$H, wherein $R^8$ is a covalent bond (—) or a spacer group optionally containing one or more heteroatoms.

In some embodiments one of R', $R^2$, or $R^3$ is methyl; in some embodiments at two of R', $R^2$, and/or $R^3$ are methyl; in some embodiments all of R', $R^2$, and $R^3$ are methyl.

In some embodiments $R^4$ is methyl (—CH$_3$).

In some embodiments $R^5$ is a saturated branched C4-C16 alkyl group. In some embodiments $R^5$ has the formula:

Exemplary compounds of general formula I are tocopherols that include alpha (α) tocopherol:

beta (β) tocopherol:

gamma (γ) tocopherol:

delta (δ) tocopherol:

Tocopherols can be commercially obtained from various sources, such as Sigma-Aldrich, St. Louis, Mo.

Also included as compounds of the general formula I are tocotrienols, such as alpha(α)tocotrienol, beta (β)tocotrienol, gamma (γ)tocotrienols, and delta (δ)tocotrienol.

The chemical structure of alpha(α)tocotrienol is shown below:

Esters of tocopherols are also contemplated, for example, where $R^6$ is —C(O)R$^7$ wherein $R^7$ is C1-C6 alkyl. An exemplary tocopherol ester is alpha (α) tocopherol acetate:

Poly(ethylene glycol) (PEG) derivatives of tocopherols are also contemplated, for example where $R^6$ is —$R^8$ ($CH_2CH_2O)_n$H, and $R^8$ is a covalent bond (—) or a spacer group optionally containing one or more heteroatoms. PEGylated tocopherol/vitamin E derivatives with molecular weights in the range of 2000-5000 Da are commercially available (e.g., from Nanocs, New York, N.Y.).

The amount of alkyl-substituted chromanol present in the liquid composition along with the bioactive agent and first biocompatible polymer can be described in various ways. In some preparations the amount of alkyl-substituted chromanol can be at a concentration of about 0.01 mg/mL or greater, or in the range of about 0.01 mg/mL to about 10 mg/mL, or about 0.05 mg/mL to about 2.5 mg/mL. For example, in some preparations the amount of alkyl-substituted chromanol can be in the range of about 0.001% to about 1.0% (w/w), in the range of about 0.01% to about 0.5% (w/w), or about 0.5% of the amount of the biologic agent (e.g., macrolide therapeutic) in the composition.

The amount of bioactive agent, first biocompatible polymer, and optionally, alkyl-substituted chromanol, can represent at least about 50% (wt), at least about 60% (wt), at least about 70% (wt), at least about 80% (wt), at least about 90% (wt), at least about 95% (wt), at least about 98% (wt), or at least about 99% (wt), of the total solids components in the first composition.

After the first composition is formed it can be contacted with a second composition that includes the second biocompatible polymer having negatively charged groups. In doing so, this provides components for the formation of an intermediate particle with second biocompatible polymer with negatively charged groups on the outer surface, and a core particle including the bioactive agent and first biocompatible polymer.

An "acid group-containing polymer" refers to polymer that has acid groups presented on the polymer chain, and which can provide negatively charged groups to the particulate. Acidic groups include, for example, sulfonic acids, carboxylic acids, phosphonic acids, and the like. Exemplary salts of such groups include, for example, sulfonate, carboxylate, and phosphate salts. Exemplary counter ions include alkali, alkaline earths metals, ammonium, protonated amines, and the like. If one or more counter ions are used, the acid groups of the acid group-containing polymer can be partially neutralized.

Exemplary carboxylic acid-group containing monomers that can be used to prepare the acid group-containing polymer, include, but are not limited to acrylic acid, methacrylic acid, itaconic acid, monomethyl itaconic acid, maleic anhydride, fumaric acid, and crotonic acid, and salts thereof. Exemplary sulfonic acid-group containing monomers that can be used to prepare the acid group-containing polymer, include, but are not limited to acrylamido-2-methylpropanesulfonic acid (AMPS), 2-(meth)acrylamido-2-methylpropane sulfonic acid, vinyl sulfonic acid, 2-sulfoethyl methacrylate, and salts thereof. Other exemplary carboxylic acid-containing monomers that can be used to prepare the acid group-containing copolymers include styrene and maleic anhydride copolymerized to produce styrene-maleic anhydride copolymer (PSMA).

Copolymers made from a combination of two or more different acid-group containing monomers can be used, or copolymers made from one or more acid-group containing monomers and one or more non-acid group containing monomers can be used. These copolymers can be random copolymers, block copolymers, graft copolymers or blends thereof.

The acid group-containing polymer may optionally be described with reference to its pH. For example, the acid group-containing polymer may have a pH in the range of about 1 to about 5, about 1.2 to about 5, about 1.5 to about 5, about 2.5 to about 5, about 2.75 to about 4.5, or about 3 to about 4.25.

The negatively charged groups can be provided by an acrylic acid polymer. As used herein an "acrylic acid polymer" refers to polymers including acrylic acid monomeric units. The acrylic acid polymer can be an acrylic acid homopolymer or a acrylic acid copolymer including acrylic acid and one or more (e.g., two, three, four, five, etc.) other monomeric units that are different than acrylic acid. In embodiments, in a poly(acrylic acid) copolymer, the acrylic acid can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater, 92.5% (mol) or greater, 95% (mol) or greater, 97.5% (mol) or 99% (mol) or greater. In exemplary embodiments, acrylic acid is present in the copolymer in the range of about 75% (mol) to about 100% (mol), about 85% (mol) to about 100% (mol), about 95% (mol) to about 100% (mol), or about 98% (mol) to about 100% (mol).

In some embodiments, an acrylic acid polymer on the outer surface of the particulate may have an average molecular weight of in the range of about 1000 kDa to about 2000 kDa, about 1200 kDa to about 1800 kDa, such as about 1500 kDa.

In some modes of preparation, the acrylic acid polymer is prepared by free radical polymerization of acrylic acid at (e.g, about a 0.8 M concentration) in deionized water. In modes where a portion of the acid groups are neutralized, a concentrated base such as NaOH is added to the acrylic acid solution. Next, an initiator such as ammonium persulfate is added with stirring. The polymerization solution can be degassed with nitrogen and stirred for hours (e.g., 12-24 hours) at an elevated temperature (e.g., greater than 50° C.). The polymer can then be polymerized against continuous flow deionized water using 12-14 K dialysis tubing, and then isolated by lyophilization.

The second composition can include the second biocompatible polymer at a desired concentration. For example, the concentration of the second biocompatible polymer, or mixture of polymers, can be in the range of about 0.001% (wt) to about 2.5% (wt), about 0.01% (wt) to about 1.5% (wt), about 0.025% (wt) to about 2.5% (wt), about 0.05% (wt) to about 1.5% (wt), or about 0.05% (wt) to about 1.25% (wt). The concentration of the concentration of the second biocompatible polymer can be adjusted to provide a desired particle size as formed in subsequent processing step. For example, in some modes of practice the size of the particle can be increased by decreasing the concentration of the second biocompatible polymer in the second composition.

The amount of second biocompatible polymer can represent at least about 50% (wt), at least about 60% (wt), at least about 70% (wt), at least about 80% (wt), at least about 90% (wt), at least about 95% (wt), at least about 98% (wt), or at least about 99% (wt), of the total solids components in the second composition. In embodiments, the second biocompatible polymer can be present in the particulate in an amount less than a combined amount of the first biocompatible polymer and bioactive agent.

Poly(acrylic acid) can be dissolved in deionized water to a concentration about 1% (wt/v). The resulting pH of the solution may be below about 5 or below about 4, such as about 3.5. The pH of the solution can optionally be increased by the addition of a base, such as sodium hydroxide or potassium hydroxide. After addition of base the resulting pH of the solution may be above about 5 or above about 6, such as in the range of 6-8. Addition of the base may increase the viscosity of the solution. The solution can be used in highly viscous form, or can be diluted to a lower polymer concentration and viscosity. Adjusting the viscosity and concentration can be useful for providing particulates of a desired size. The selection of a polymer molecular weight range can also affect the viscosity of the composition. Further, a solvent, such as one that can dissolve the first biodegradable biocompatible polymer can be added to the poly(acrylic acid) composition prior to addition of the dissolved first polymer and drug and emulsification. For example, the solvent such as ethylacetate can be added in an amount of about 5-10% (v/v), e.g., up to saturation, to the poly(acrylic acid) composition which can faciliate formation of the particulates.

A processing step can include contacting the first solution (including the bioactive agent and first biocompatible polymer) with the second solution (including the second biocompatible polymer). In preferred modes of practice an amount of first solution is added to a larger volume of second solution, wherein the mixture is an emulsion with the first solution as the continuous phase. The mixture can be formed at a desired temperature, such in the range of about 5° C.-50° C., such as at room temperature of an ambient temperature.

In modes of practice, a volume of the first composition that is less than about 25% of the volume of the second composition is added to the second composition. More preferably a volume of the first composition is less than about 15%, less than about 10%, or less than about 5%, such as a volume in the range of about 0.1% to about 5%, of the volume of the second composition is added to the second composition.

Addition of the first composition to the second composition can be performed with agitation, preferably high speed blending. In some modes of practice, the addition can be performed with sufficient agitation and in a manner to rapidly mix the first and second compositions to form an emulsion. In preferred modes of practice the mixture is emulsified using a high-speed blender (e.g., greater than 1000 RPM). Blending can be performed for a desired period of time, e.g. seconds, tens of seconds, a minute, or minutes.

In some modes of practice, an organic solvent, or mixture of organic solvents (i.e., without bioactive agent and first biocompatible polymer), is added to the second composition prior to addition of the first composition. The organic solvent can be the same, or a different organic solvent that is miscible with the organic solvent that dissolves the bioactive agent and first biocompatible polymer.

Mixing of the first and second solutions can be performed in a desired receptacle, such as one formed of plastic, glass, or metal, the inner surfaces of which can optionally be treated to minimize or eliminate any non-specific adsorption of the components that form the particulate to the surface. Exemplary thermoplastics receptacles are fabricated from polypropylene, polystyrene, poly(tetrafluoroethylene) (PTFE), and perfluoroalkoxy (PFA) polymers, such as Teflon™ and Neoflon™.

After the first and second compositions have been blended to form an emulsified composition, the emulsified composition can be added to a larger volume of an aqueous solution to form particulates. For example, the emulsified composition can be added to an aqueous composition of a volume at least two times greater than the volume of the emulsified composition, such as about five times greater. The mixture can be stirred such as by using an overhead stirrer, or stirring equipment such as stir bars. The mixture can be stirred for a desired period of time to provide desired particle formation, such as for minute, tens of minutes, an hour, or hours. Stirring and particle formation can take place at a desired temperature, such in the range of about 5° C.-50° C., such as at room temperature of an ambient temperature.

Formation of particulates can be determined visually, or by other methods, such as by spectrometry. Spectrophotometric measurements may also be useful for determining the optimal conditions for particulate formation. After stirring the formed particles can be collected or isolated from the aqueous solution, such as by filtration or centrifugation. The particles can be washed and then dried such as by lyophilization.

Particles that are formed can have a spherical or substantially spherical shape. However, other non-spherical shapes such oblong or irregular may be observed within a set of particles. The particles can have a size in the range of about 100 nm to 100 μm in diameter, or more typically about 500 nm to about 50 μm in diameter. The use of a second composition having a defined polymer concentration can provide particle preparations with less disperse size ranges, such as about 1 μm to about 10 μm in diameter, about 2 μm to about 7 μm in diameter, about 5 μm to about 25 μm in diameter, or about 8 μm to about 22 μm in diameter. More concentrated solutions (e.g., 1% second polymer) may produce particles or smaller size ranges, whereas less concentrated solutions (e.g., 0.1% second polymer) may produce particles or larger size ranges.

Particles that include the bioactive agent, first biocompatible polymer, and second biocompatible polymer, and optional excipient can be described in terms of the weight amount of each component in the particle.

In some embodiments, the bioactive agent (e.g., rapamycin) is present in an amount in the range of about 10% to about 90% (wt), the first biocompatible polymer (e.g., poly(ether ester) multiblock copolymers) is present in an amount in the range of about 10% to about 90% (wt), the second biocompatible polymer (e.g., poly(acrylic acid)) is present in an amount in the range of about 5% to about 75% (wt), and optionally one or more excipients (e.g., tocopherol) is/are present in an amount in the range of about 0.0001% to about 5% (wt).

In some embodiments, the bioactive agent (e.g., rapamycin) is present in an amount in the range of about 10% to about 50% (wt), the first biocompatible polymer (e.g., poly(ether ester) multiblock copolymers) is present in an amount in the range of about 25% to about 75% (wt), the second biocompatible polymer (e.g., poly(acrylic acid)) is present in an amount in the range of about 10% to about 60% (wt), and optionally one or more excipients (e.g., tocopherol) is/are present in an amount in the range of about 0.001% to about 1% (wt).

In some embodiments, the bioactive agent (e.g., rapamycin) is present in an amount in the range of about 20% to about 40% (wt), the first biocompatible polymer (e.g., poly(ether ester) multiblock copolymers) is present in an amount in the range of about 40% to about 70% (wt), the second biocompatible polymer (e.g., poly(acrylic acid)) is present in an amount in the range of about 15% to about 35% (wt), and optionally one or more excipients (e.g., tocopherol) is/are present in an amount in the range of about 0.01% to about 0.05% (wt).

The particulates can then be associated with one or more cationic agents. Exemplary cationic agent classes include cationic lipids, cationic polymers, and lipidoids. Cationic agents used in embodiments herein include compounds containing a portion having a positive charge in aqueous solution. The positive charge can allow the cationic agent to associate with the negative charge of the cationic polymer.

In some embodiments the cationic agents comprises a water soluble poly(alkyleneimine). The water soluble poly (alkyleneimine) can be a compound of that include repeating units of formula II:

in which R may be a hydrogen atom or a group of formula n is an integer between 2 and 10, preferably n is between 2 and 5; and p and q are integers, with the sum of p+q being that the average molecular weight of the polymer is between 100 and $10^7$ Da, preferably between $10^3$ and $10^6$ Da. Polymers that include repeating units of formula II include homopolymers and heteropolymers, and linear polymers and branched polymers.

Polyethyleneimine (PEI; also polyaziridine) and polypropyleneimine (PPI) polymers are exemplary polymers. PEI of various molecular weights, such as 50,000 Da (PEI50K) and 800,000 Da (PEI800K), are commercially available.

Other cationic polymers include, but are not limited to, poly-vinylamine, polyallylamine, polylysine, primary amine-group containing polyacrylates or polyacrylamides such as poly(aminopropylmethacrylate) (i.e., poly-APMA).

Cationic agents can specifically include cationic polymers. Cationic agents can also include polycation-containing cyclodextrin, histones, protamines, cationized human serum albumin, aminopolysaccharides such as chitosan, peptides such as poly-L-lysine, poly-L-ornithine, and poly (4-hydroxy-L-proline ester, and polyamines such as polyethylenimine (PEI; available from Sigma Aldrich), polypropylenimine, polyamidoamine dendrimers (PAMAM; available from Sigma Aldrich), cationic polyoxazoline and poly(beta-aminoesters). Cationic agents can also specifically include cationic lipidoids (as described by K. T. Love in the publication PNAS 107, 1864-1869 (2010)). Other exemplary cationic polymers include, but are not limited to, block copolymers such as PEG-PEI and PLGA-PEI copolymers.

In some embodiments the cationic agent can be an alkylated quaternary ammonium salt. The alkylated quaternary ammonium salt can be a compound of general formula III:

wherein $R^1$, $R^2$, $R^3$, and $R^4$ are independently selected from H and linear, branched, and cyclic alkyl groups, wherein the total number of carbon atoms among $R^1+R^2+R^3+R^4$ is an integer in the range of 6 to 30, or more preferably 10 to 22; and X is a halogen anion. In exemplary embodiments: $R^1$, $R^2$, and $R^3$ are methyl (—$CH_3$) groups; $R^4$ is a linear or branched alkyl group having 10 to 22 carbon atoms, or 12 to 20 carbon atoms.

Exemplary compounds of formula III include cetyltrimethylammonium bromide (CTAB), cetyltrimethylammonium chloride (CTAC), cetyltrimethylammonium hydrosulfate (CTAS), tetradecyltrimethylammonium bromide (TTAB), and octadecyltrimethylammonium bromide (OTAB).

In some embodiments, cationic agent can include those having the general formula X-Y, wherein X is a radical including a positively charged group in aqueous solution at neutral pH and Y is a radical exhibiting hydrophobic properties. In some embodiments, the cationic agent can include a hydrophilic head and a hydrophobic tail, along with one or more positively charged groups, typically in the area of the hydrophilic head.

Cationic agents can specifically include cationic lipids and net neutral lipids that have a cationic group. Exemplary lipids can include, but are not limited to, 3β-[N—(N',N'-dimethylaminoethane)-carbamoyl]cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Additional lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE).

Cationic agents containing a portion having a positive charge in aqueous solutions at neutral pH include the following Compounds (A-I):

Compound A

-continued

Compound B

Compound C

Compound D

Compound E

Compound F

Compound G

Compound H

Compound I

Additionally, other cationic agents include structures of the general Formula I:

Formula I

TABLE 1

Values for Variables x + z,
y and R for Compounds J-R of Formula I.

| Compound | x + z | y | R |
|---|---|---|---|
| Compound J | 6 | 12.5 | $C_{12}H_{25}$ |
| Compound K | 1.2 | 2 | $C_{12}H_{25}$ |
| Compound L | 6 | 39 | $C_{12}H_{25}$ |
| Compound M | 6 | 12.5 | $C_{14}H_{29}$ |
| Compound N | 1.2 | 2 | $C_{14}H_{29}$ |
| Compound O | 6 | 39 | $C_{14}H_{29}$ |
| Compound P | 6 | 12.5 | $C_{16}H_{33}$ |
| Compound Q | 1.2 | 2 | $C_{16}H_{33}$ |
| Compound R | 6 | 39 | $C_{16}H_{33}$ |

Cationic agents, such as those listed above, can generally be prepared by the reaction of an appropriate hydrophobic epoxide (e.g. oleyl epoxide) with a multi-functional amine (e.g. propylene diamine). Details of the synthesis of related cationic agents are described by K. T. Love in the publication PNAS 107, 1864-1869 (2010) and Ghonaim et al., Pharma Res 27, 17-29 (2010).

In some embodiments the cationic agent is a vinyl amine polymer, such as poly(N-vinyl amine) (pNVA). A vinyl amine polymer can include copolymers, terpolymers, including N-vinyl amine and/or N-vinyl formamide (NVF) subunits. An exemplary vinyl amine polymer is according to Formula I, wherein x is from 1 to 100 mole percent, and y is from 0 to 99 mole percent.

Formula I

An N-vinyl formamide (NVF) homopolymer can be treated with a base such as sodium hydroxide to cause partial or full hydrolysis of NVF residues and formation of the N-vinyl amine residue.

Optionally, one or more other monomers can be present in a vinyl amine polymer, such as vinyl esters, (meth)acrylate esters, vinyl imidazoles, vinyl pyridines, vinyl alcohols, vinyl halides, acrylonitriles, acrylamides, vinyl silanes, styrenes, and the like.

In some embodiments, the additional monomer is a nitrogen-containing monomer such as 1-vinyl-2-pyrrolidone. In some embodiments, the vinyl amine polymer can include a terpolymer having Formula II, wherein x is from 1 to 100 mole percent, y is from 0 to 99 mole percent, and z is from 0 to 99 mole percent.

In some embodiments, the vinyl amine polymer component is partially or fully hydrolyzed.

Preparation of (NVF-co-NVP) polymers with varying molar ratios of 1-vinyl-2-pyrrolidinone (NVP) and N-vinyl-formamide (NVF) have been described, in U.S. Pub. No. 2014/0336571 (Slager, et al.), the teaching of which is incorporated herein by reference.

In yet other embodiments cationic agents can include moieties used to condense nucleic acids (for example lipids, peptides and other cationic polymers). In some instances these cationic agents can be used to form lipoplexes and polyplexes.

A composition that includes one or more cationic agents at a desired concentration can be prepared. The cationic agent-containing composition can be an aqueous composition having a pH so the cationic agent has a positive charge in solution. For example, the pH of the composition can be below about 10, and is preferably in the range of about 6 to about 8. The concentration of the cationic agent in the composition can be chosen to provide coated particulates as desired, and can be based on the amount of particulates that are added to the composition. For example, the concentration of the cationic agent, or mixture of cationic agents, is in the range of about 1% (wt) to about 25% (wt), about 2% (wt) to about 20% (wt), or about 5% (wt) to about 15% (wt).

In modes of practice, an amount of particles is added to the cationic agent-containing composition sufficient to associate the cationic agent with the negatively charged surface of the bioactive agent-containing particles and provide the particles with a positive charge. The charge is generally referred to as the zeta potential (also known as the electrokinetic potential). A particle's zeta potential refers to the potential difference between the ionic charge of the particle surface and the bulk charge of the fluid composition, which includes the fluid carrier and component(s) dissolved therein, that surrounding the particles. The pH of the liquid composition can affect the zeta potential of the particles, with the particle's isoelectric point being the pH at which the zeta potential is zero. As the pH is increased or decreased away from the isoelectric point, the surface charge (and hence the zeta potential) is correspondingly decreased or increased (to negative or positive zeta potential values). Preferably the charge on the particles can be stable, such as that it is not substantially changed by washing, dilution, filtration, or the like.

The cationic agent can be chosen and added to the particle-containing composition in an amount so the cationic agent associates with the surface of the particle via electrostatic charges, and further provides sufficient cationic groups to provide the particle with a positive zeta potential at a pH in the range of about 6-8. In modes of preparing the composition, most of, or all of, the cationic agent present in the composition may associate with the particles. Optionally, the particles in the composition can be described in terms of a potential value.

In modes of practice, a desired amount of particles are added to the cationic agent-containing composition to provide the particles with a positive zeta potential. For example, the composition can be formed with a weight ratio of particles to cationic agent in the range of about 50:1 to about 1:1, about 25:1 to about 4:1, about 15:1 to about 6:1, or about 15:1 to about 6:1.

The particulates can be described with regards the physical or morphological properties of the particle. The particles can have a central "core" of bioactive agent and first biocompatible polymer, and then an outer "shell" of material around the core that includes the second biocompatible polymer and the cationic agent. In embodiments, in the particle most of, or all of, the second biocompatible polymer may be between the core and the cationic agent, which can represent the outermost material of the particle. In some cases, shell can have a thickness that is less than the overall diameter of the particulate per se. The shell of the particulate can promote transfer of the particulate to a tissue after placement within a patient, and also modulate release of bioactive agent in the body. Material of the particulate may provide a mechanism for the sustained delivery or prolonged release of the bioactive agent in a subject.

The particulates of the present disclosure can be delivered to or placed in contact with a site within the body for the therapeutic treatment of a medical condition. Generally, when placed in contact with a body fluid the bioactive agent in molecular form will be released from the particulate, which can provide a bioactive effect locally or systemically in the body.

The bioactive agent-containing particulates can be prepared to dissolve and release macrolide therapeutic in an aqueous environment, such as body fluid. Release can involve dissolution of the cationic agent and second biocompatible polymer (e.g., acidic group-containing polymer), and dissolution or degradation, or both, of the first biocompatible polymer.

In some embodiments, the bioactive agent-containing particulates can be included in a therapeutic liquid delivery composition. The liquid composition can be prepared for the delivery of the particulates via injection into a target location in the body. For example, the particulate compositions can be formulated for subcutaneous, intramuscular, intravenous, intrathecal, intraperitoneal, or intraocular injections.

The bioactive agent-containing particulates can be used in a composition and/or method as described in commonly assigned U.S. Provisional Patent Application Ser. No. 62/316,161 entitled "Localized Treatment of Tissues Through Transcatheter Delivery of Active Agents," to Slager, J., and filed on Mar. 31, 2016, the teaching of which is incorporated herewith, wherein said application discloses exemplary methodologies for isolating organs and perfusing the organs with bioactive agent-containing compositions.

In some aspects, the particulates are associated with a system that controls the release of the particulates and bioactive agent to the body. For example, the particulates can be associated with a portion of an implantable medical device. In some arrangements, the particulates are included in an internal reservoir of an implantable medical device. The reservoir can be covered with one or more apertures, or can have a membrane. Particulates can be released from the reservoir exiting the device through the apertures or membrane, upon which the particulates are transferred to a tissue and/or fluid in a subject. Exemplary medical devices having apertures capable of releasing therapeutic are described in various references, such as described in commonly assigned US2008/0081064 (Anderson, et al.) In some aspects, the particulates are associated with a polymeric matrix that can be placed or formed at a target location in the body. For example, the particulates can be entrained or entrapped within the polymeric matrix, associated with the surface of a polymeric matrix, or combinations thereof. The polymeric matrix can modulate release of the particulate by one or more modes of release modulation.

The polymeric matrix can be in the form of an in-situ formed polymeric matrix, or can be associated with an implant. For example, the polymeric matrix can also be associated with an implantable medical device, such as in the form of a coating on a surface of the device or a matrix within the device. The polymeric matrix can be biostable, biodegradable, or can have both biostable and biodegradable properties. The polymeric matrix can be formed from synthetic or natural polymers.

The particulates may be associated with a lipid coating that includes one or more fatty acids, such as described in US2012/0165786 (Chappa et al.). For example, the particulates may be present in a coating on a balloon and covered associated with a lipid coating having a melting or softening point greater than room temperature and less than body temperature of a subject. The lipid coating may protect the particulates during insertion of the balloon catheter in the body and promote its release at the delivery site. An exemplary coating includes a mixture of dodecanoic acid and oleic acid e.g., (at a 1:1 wt ratio) applied over the particulates.

The particulates can be associated with a medical device, such as in a polymeric matrix associated with the medical device. In some cases, a particulate-containing coating can be formed on the surface of a medical article that can be introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects, the particulates, such as those containing a macrolide like rapamycin, are associated with a balloon catheter, such as associated with a polymeric coating on a portion, or all of, the balloon surface. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. The particulates may be associated with a balloon catheter device such as described in US2012/0004605 (Chappa) which includes a sleeve having a plurality of openings disposed over a coating on the balloon surface, with the sleeve adapted to expand between a compressed state and an enlarged state and to return to the compressed state. The particulates may be associated with a balloon catheter device such as described in US2012/0172839 (Chappa) which describes a catheter assembly with inner and outer expandable structures, and a therapeutic composition therebetween, with outer expandable structure having openings and photolabile seal scissile coatings. The particulates may be associated with a balloon catheter device such as described in US2012/0083733 (Chappa) which describes a catheter assembly with expandable structure with guard bonded to an expandable structure having reservoirs containing coating with active agent.

Balloon catheters generally include four portions, the balloon, catheter shaft, guidewire, and manifold. In a balloon catheter an elongated catheter shaft with the inflatable balloon can be attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion can be then fed over the guidewire until the balloon reaches the target location in the vessel. The balloon can be then inflated when the catheter reaches the targeted constriction to thereby apply the requisite mechanical force to cause vessel dilation. The manifold can also control the fluid introduction within shaft for expansion of the balloon. The balloon is typically inserted into the arterial lumen of a patient and advanced through the lumen in an unexpanded state.

The balloon can be formed from any material, or combination of materials, capable of expanding, and suitable for use within the body. The balloon can be made from an elastomer, which can be a thermoplastic polymer with elastic properties. Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, and polyether-polyamide copolymers.

The balloon can be made of a single elastomeric material, or a combination of materials. The balloon can be manufactured by an extrusion process, so that the elastic portion can be a single layer of material, or co-extruded to form a multi-layered material.

The elastic portion (balloon) can have a thickness suitable for a desired application and device. For example, an exemplary thickness of an elastic portion can be in the range of about 0.005 mm to about 0.25 mm, or about 0.005 mm to about 0.1 mm, or about 0.005 mm to about 0.05 mm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon.

In some aspects, a balloon catheter comprises a balloon and bioactive agent-containing particulates associated therewith can be formed upon can be a macroscopically smooth, microporous, flexible, elastic tubular prosthetic device made from a substantially non-elastic woven fabric tube as described in U.S. Pat. No. 4,652,263. The exterior of the tube can be an easily deformed, macroscopically smooth surface having a multiplicity of interstices, or apertures, among the threads and among the fibers of the threads.

In some embodiments, apertures in the balloon can have openings of predetermined sizes suitable for a biocompatible liquid to be released and to affect release of transfer of the particulates, e.g., macrolide-containing particulates of the disclosure, from the balloon surface. In some aspects the apertures have a size in the range of about 0.0025 mm to about 2.5 mm, about 0.005 mm to about 1 mm, or about 0.01 mm to about 0.5 mm. The apertures in the balloon can be of any shape or combination of shapes, although a preferred shape of the apertures can be round. Other shapes such as oval and polygonal (triangular, square, rectangular, hexagonal) shapes are contemplated.

The balloon on which a coating with bioactive agent-containing particulates can be formed can be commercially obtained, for example, from Atrium Medical (e.g., the ClearWay™ RX catheter having a 0.014" guidewire, 6 & 7 Fr guide catheter, 1-4 ATM Infusion Pressure, and 134 cm catheter working length).

In modes of practice a composition that includes the bioactive agent-containing particles associated with cationic agent is applied to a hydrophilic coating on a balloon surface. An exemplary balloon coating includes one or more hydrophilic polymer(s), such as polyvinyl pyrrolidone and/or polyacrylamide, along with photoreactive groups pendent from the hydrophilic polymer, from a crosslinker, or both.

Coatings that include polyvinyl pyrrolidone and/or polyacrylamide, and poly(acrylic acid) are described in US2014/0193474.

Crosslinking agents that can be included in a coating on which the particulates are applied can include those having formula Photo1-LG-Photo2, wherein Photo1 and Photo2 independently represent at least one photoreactive group and LG represents a linking group comprising at least one silicon or at least one phosphorus atom, wherein the degradable linking agent comprises a covalent linkage between at least one photoreactive group and the linking group, wherein the covalent linkage between at least one photoreactive group and the linking group is interrupted by at least one heteroatom. See U.S. Pat. No. 8,889,760 (Kurdyumov, et al.), the disclosure of which is incorporated herein by reference. Further crosslinking agents can include those having a core molecule with one or more charged groups and one or more photoreactive groups covalently attached to the core molecule by one or more degradable linkers. See U.S. Publ. Pat. App. No. 2011/0144373 (Swan, et al.), the disclosure of which is incorporated herein by reference.

In some embodiments, the crosslinking agent can have a molecular weight of less than about 1500 kDa. In some embodiments the crosslinking agent can have a molecular weight of less than about 1200, 1100, 1000, 900, 800, 700, 600, 500, or 400.

In some embodiments, the crosslinking agent comprises a linking agent having a formula selected from:

(a)

[Structure with benzoyl groups connected via Si-Si linkage with substituents $R^1, R^2, R^3, R^4, R^5, R^6, R^7, R^8, R^9$ and X groups]

wherein R1, R2, R8 and R9 are any substitution; R3, R4, R6 and R7 are alkyl, aryl, or a combination thereof; R5 is any substitution; and each X, independently, is O, N, Se, S, or alkyl, or a combination thereof;

(b)

[Structure with benzoyl groups connected via Si linkage with substituents $R^1, R^2, R^3, R^4, R^5$ and X groups]

wherein R1 and R5 are any substitution; R2 and R4 can be any substitution, except OH; R3 can be alkyl, aryl, or a combination thereof; and X, independently, are O, N, Se, S, alkylene, or a combination thereof;

(c)

[Structure with benzoyl groups connected via P-P linkage with substituents $R^1, R^2, R^3, R^4, R^5, R^6$ and X groups]

wherein R1, R2, R4 and R5 are any substitution; R3 is any substitution; R6 and R7 are alkyl, aryl, or a combination thereof; and each X can independently be O, N, Se, S, alkylene, or a combination thereof; and (d)

[Structure of bis(4-benzoylphenyl) phosphate sodium salt]

In a particular embodiment, the crosslinking agent can be bis(4-benzoylphenyl) phosphate.

Particle coating formulations that include the cationic and bioactive agent-containing particulates are applied to the hydrophilic coating. Knowing the drug loading in the particulates, a predetermined quantity of particulates can be applied to the hydrophilic coating.

For example, an amount of about 1 µg/mm$^2$ or greater, about 2 µg/mm$^2$ or greater, such as about 2.5 µg/mm$^2$ to about 10 µg/mm$^2$ of particulates per unit area can be applied to the hydrophilic coating. The particles can provide a desired amount of bioactive agent per balloon, based on the content on the bioactive agent in the particulates. For example, for rapamycin a total amount per balloon can be about 100 µg or greater, such as in the range of about 100 µg to about 500 µg.

After the particulates are applied to the device surface the coating can be dried, such as by using a stream of heated nitrogen gas. Further drying of the balloon coating can be performed, along with other manipulation (e.g., balloon folding) in preparation for insertion into a subject.

In a treatment method, the balloon can be inflated using a fluid, which can be injected through an inflation port. The mechanics of fluid transfer and introduction within balloons vary according to the specific design of the catheter, and are well know in the art.

A balloon catheter with bioactive agent-containing particulates can be used in a balloon angioplasty procedure. Balloon angioplasty can be carried out for the treatment of diseased arteries to reduce atherosclerotic stenosis or to recanalize occluded arteries. In such a procedure, obstructed intraluminal passages are reopened or dilated by inflation of the balloon at the occluded site. According to the disclosure, balloon catheter having a particulate associated balloon portion can be inserted percutaneously into a luminal passage of a patient, such as an artery, vein, or airway. Once inserted, the balloon can be advanced to the desired treatment site, where the balloon can be inflated to dilate the luminal passage.

In some modes of practice, upon inflation of the balloon, at least a portion of the particulates that are associated with the surface of the balloon are transferred to the tissue of lumenal arterial wall at the target site. The cationic agent can facilitate transfer of the particulates to a tissue.

For example, in aspects wherein the particulates are included in an expandable coating on the surface of the balloon, the inflation of the balloon can stretch the coating. The coating on the surface of the balloon can undergo physical changes that promote the release of the particulates. Upon insertion in a subject, a coating that is in the form of a flexible hydrogel matrix can become more hydrated, resulting in a loosening of the matrix material around the particulates. Also, the stretching of the coating (upon balloon expansion) can cause it to effectively become thinner than the coating on the balloon in an unexpanded state. In addition, the stretching of the coating can create pores in the coating from which the particulates can escape. The hydration, thinning of the coating and/or the creation of the pores can effectively cause the macrolide particulates to "pop out" of the coating upon balloon expansion. Further, the cationic agent associated with the particulates can promote a bulk movement of the particles away from the coating and to the tissue. In turn, this can ensure that more of the particles, and in turn, more of the bioactive agent that is on the balloon moves off the coating and to the patient tissue.

The particulates that are transferred can adhere to the arterial tissue at the target site. Accordingly, the particulates can release bioactive agent at the target site, which can have a therapeutic effect on the tissue. The bioactive agent, such as a macrolide therapeutic, at the target site can be useful to control tissue response after balloon dilation. For example, the particulates can release sirolimus that can inhibit neointimal proliferation at the dilated site.

In some modes of treatment, macrolide particulates can be used to release the bioactive agent at a target site in a sustained profile. The first and or second biocompatible 
polymer(s) can modulate release over an extended and therapeutically useful time period.

Bioactive agent, such as a macrolide therapeutic released from the particulates, can be used to treat specific diseases. For example, non-antibiotic macrolide particles can be used in various medical methods such as providing immunosuppressant activity to prevent rejection in organ transplantation. Non-antibiotic macrolides, such as rapamycin, can also be used to prevent hyperplasia and restenosis otherwise associated with inflammation, fibrosis, and thrombosis in tissues responses.

Antibiotic macrolide particles can be used to treat bacterial infections. For example, treatment can be carried out to reduce infection caused by gram-positive bacteria such as *Streptococcus pneumoniae* and *Haemophilus influenzae*, which may soft-tissue and the respiratory tract. Antibiotic macrolides can be used to treat infections caused by organisms such as *Chlamydia*, enterococci, *Legionella pneumophila, mycoplasma*, mycobacteria, *rickettsia*, pneumococci, streptococci, and staphylococci.

Example 1

Microspheres of Rapamycin with GAPEGCL-GALA in 1% w/v PAA Solution

Poly(acrylic acid) (Carbopol 980 NF) 10 gram was added to 1 L deionized water and stirred at room temperature for 24 hours. 1 M NaOH was added raising the pH from 3.5 to 6.8, obtaining a very viscous solution (1% w/v). 100 mL of this solution was diluted in 1 L deionized water to obtain a 0.1% w/v solution.

Microspheres including rapamycin were prepared by dissolving 100 mg rapamycin (LC-Labs) and 200 mg GAPEGCL-GALA in 6 mL ethylacetate. 10 μL of an α-tocopherol succinate solution in ethanol at 50 mg/mL was added to the mixture. In a beaker covered with aluminum foil, 6 mL ethylacetate was added to 100 mL of the 1% w/v polyacryllic acid solution in water and stirred at room temperature for 15 minutes (continuous phase). 3 mL of the polymer-drug solution was homogenized in 100 mL of the continuous phase using a Silverson mixer at 5000 rpm for one minute. The resulting emulsion was poured in 500 mL deionized water and stirred for one hour at 400 rpm. Particles were isolated by centrifugation (10.000 rpm for 15 minutes), washed 3× with deionized water and lyophilized.

Example 2

Microspheres of Rapamycin with GAPEGCL-GALA (GP0x) in 0.1% w/v PAA Solution

In a beaker covered with aluminum foil 6 mL ethylacetate was added to 100 mL of the 0.1% w/v poly(acrylic acid) solution in water (per example 1) and stirred at room temperature for 15 minutes (continuous phase). 3 mL of the polymer-drug solution (as prepared in example 1) was homogenized in 100 mL of the continuous phase using a Silverson mixer at 5000 rpm for one minute. The resulting emulsion was poured in 500 mL deionized water and stirred for one hour at 400 rpm. Particles were isolated by centrifugation (10,000 rpm for 15 minutes), washed 3× with deionized water and lyophilized.

Samples of the microspheres prepared in examples 1 and 2 were deposited on a glass slide and imaged with SEM. Estimate sizes of microspheres that were obtained: 1% PAA: 3-5 μm spheres; 0.1% PAA: 10-20 μm spheres.

Example 3

Analysis of microspheres of rapamycin with GAPEGCL-GALA Samples of the prepared microspheres (examples 1 and 2) were weighed and dissolved in acetonitrile at 1 mg/mL. The solutions were diluted to a rapamycin concentration of 25 μg/mL based on a theoretical drug load of 33% w/w and analyzed by HPLC. Results are shown in Table 2.

TABLE 2

| Sample ID | Aver (μg) | stdev | Drug load (%) |
|---|---|---|---|
| Rapamycin/0.5% a-Toc/GL0x 1:2 in 0.1% PAA cont. phase theor. 24.88 μg drug | 20.22 | 0.10 | 27.0 |
| Rapamycin/0.5% a-Toc/GL0x 1:2 in 0.01% PAA cont. phase theor. 24.88 μg drug | 21.26 | 0.29 | 28.3 |

Example 4

Particle adsorption from suspensions in the presence of PEI Matrigel® coated 96-well plates (Corning) were conditioned with 100 μL ECM cell medium for 1 hour at 37° C. Suspensions were prepared of 11 mg/mL microspheres in an aqueous solution of PEI 70 kDa (Polysciences) at 1 mg/ml or 2 mg/mL, the pH of the solutions being adjusted to pH 7 with HCl. 5 μL of the formulations was pipetted in the 100 μL medium in wells of the Matrigel® coated well-plate and left for 3 minutes. All wells were then rinsed 3 times with 200 μL PBS. Rapamycin adsorbed to the 96-well surface was dissolved in acetonitrile/0.1% AcOH and quantified by HPLC. Results are shown in FIG. 1.

Example 5

Ex-Vivo Testing with Rapamycin Containing Microspheres

The following nylon balloon parts were used in all studies: 20×3.5 mm. Hydrophilic basecoats (R) were deposited onto the nylon balloon surfaces. The hydrophilic basecoat solution included 6.25 g/L polyvinyl pyrrolidone (PVP) with benzoylbenzoic acid groups; 1.25 g/L polyacrylamide; 2.5 g/L PVP (K90); and 0.05 g/L photo-crosslinker; in a solvent solution of 85:15 water/isopropanol. After coating the basecoat material was dried at room temperature for 15 minutes and then irradiated with UV light for 3 minutes.

The following 92:8 w/w formulations were made (microspheres at 100 mg/mL and branched PEI of 70 kDa molecular weight at 10 mg/mL end concentrations):

a) Microparticles made in 1% PAA with PEI 750 kDa at pH 7 b) Microparticles made in 0.1% PAA with PEI 750 kDa at pH 7

An amount of 6 μg/mm$^2$ microspheres for coating on the balloons was attempted over 15 mm of the balloon surface (which is about 275 μg rapamycin per balloon, based on 28% drug load of the particles). The microspheres containing coating mixtures were applied on top of the cured hydrophilic basecoat (R) by means of a positive displacement pipette and dried in a stream of heated nitrogen gas.

All balloon parts were further dried over night at room temperature, folded, pleated and sheathed in a nylon sheath. The coated and folded parts were subsequently placed in a 55° C. oven for 1 hour.

Figure 1:
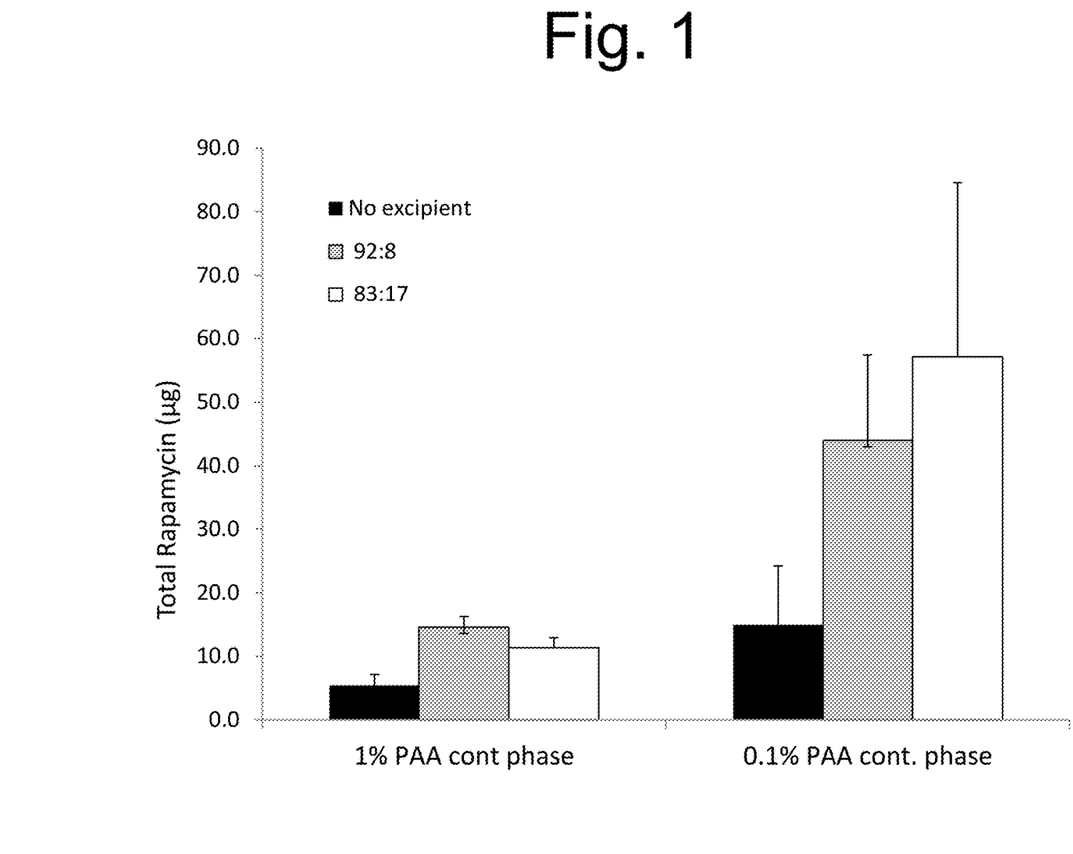
FIG. 1 is a graph showing amounts of rapamycin from cationic polymeric particulates transferred to a synthetic extracellular matrix (ECM)-coated surface.
Figure 2:
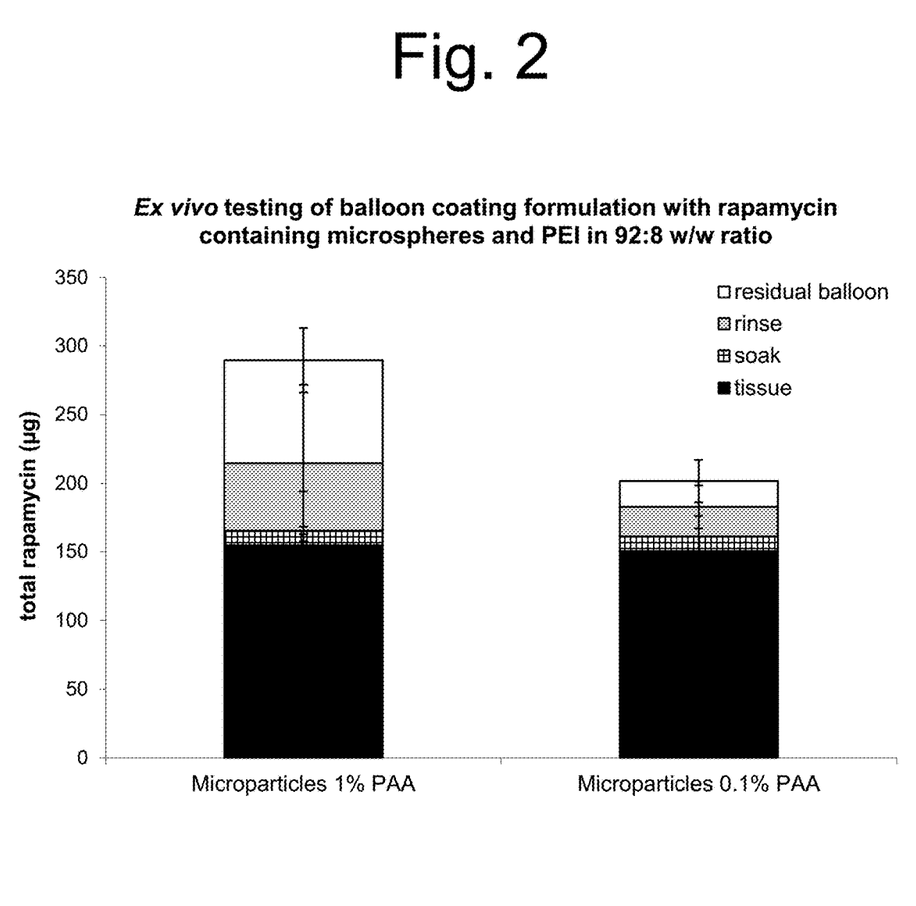
FIG. 2 is a graph showing amounts of rapamycin from cationic polymeric particulates transferred from a hydrogel coating on a nylon balloon to arterial tissue.

Release of the microspheres from the coated balloon part was then assessed according to the following procedure. Excised pig coronary arteries (Pel-Freez Biologicals) were prepared and kept at 37° C. Upon removal of the sheaths from the balloons, the balloons were soaked in PBS at 37° C. for 30 seconds and then removed from the PBS (acetonitrile was then added to the PBS at a 3:1 ratio by volume in order to extract the rapamycin). The resulting PBS and methanol solution was tested for rapamycin content using HPLC ("Soak in PBS for 30 Seconds"). Next, the balloon was expanded in the artery tissue at 60-80 psi for 30 seconds at 37° C. and after deflation and removal of the balloon, the artery tissue was rinsed with PBS at 37° C. (acetonitrile was then added to the PBS at a 3:1 ratio by volume in order to extract the rapamycin). The resulting PBS and methanol solution was tested for rapamycin content using HPLC ("Rinse after Transfer"). After removal of the balloon from the tissue and rinsing of the tissue, the tissue was placed in an acetonitrile/0.1% acetic acid solution. The resulting acetonitrile and acetic acid solution was tested for rapamycin content using HPLC ("Drug Transfer to Tissue"). The balloon was also placed in acetonitrile and 0.1% acetic acid solution. The resulting acetonitrile and acetic acid solution was tested for rapamycin content using HPLC ("Drug Retained on Balloon"). Results are shown in FIG. 2.

What is claimed is:

1. A bioactive agent delivery composition comprising
   (a) a bioactive agent-containing particulate comprising:
      a core particle comprising a bioactive agent and a first biocompatible polymer; and
      a layer around the core particle comprising a second biocompatible polymer and that comprises negatively charged groups,
      wherein the second biocompatible polymer is more water soluble than the first biocompatible polymer; and
   (b) a cationic agent associated with the negatively charged groups of particulate, which provides the particulate with a positive zeta-potential.

2. The bioactive agent delivery composition of claim 1 wherein the first biocompatible polymer is a biodegradable polymer.

3. The bioactive agent delivery composition of claim 2 wherein the first biocompatible polymer is an aliphatic polyester co-alkylene oxide block copolymer.

4. The bioactive agent delivery composition of claim 1 wherein the first biocompatible polymer is present in the particulates in an amount in the range of 10% to 90% (wt).

5. The bioactive agent delivery composition of claim 1 wherein the bioactive agent is present in the particulate in an amount in the range of 10% to 90% (wt).

6. The bioactive agent delivery composition of claim 1 wherein the bioactive agent is a macrolide or a taxane.

7. The bioactive agent delivery composition of claim 1 wherein the particulate further comprises an alkyl-substituted chromanol.

8. The bioactive agent delivery composition of claim 1 wherein the particulate is spherical in shape.

9. The bioactive agent delivery composition of claim 1 wherein the second biocompatible polymer is formed from a composition comprising an acid group-containing monomer.

10. The bioactive agent delivery composition of claim 9 wherein the acid groups are partially neutralized.

11. The bioactive agent delivery composition of claim 1 wherein the second biocompatible polymer is present in the particulate in an amount less than a combined amount of the first biocompatible polymer and bioactive agent.

12. The bioactive agent delivery composition of claim 1 wherein the cationic agent is selected from the group consisting of cationic lipids, cationic polymers, and lipidoids.

13. The bioactive agent delivery composition of claim 1, wherein the cationic agent is present in the composition in an amount in the range of 1% to 25% (wt).

14. The bioactive agent delivery composition of claim 1 wherein the particulates have a size of less than 25 μm.

15. A medical device having a surface associated with the bioactive agent delivery composition of claim 1.

16. The medical device of claim 15, wherein the balloon is an angioplasty balloon.

17. The medical device of claim 15 wherein the surface further comprises a hydrogel matrix and the composition is associated with the hydrogel matrix.

18. A method for treating a subject comprising placing a bioactive agent delivery composition of claim 1 in a subject, wherein the bioactive agent released from the particulates treats a condition in the subject.

19. A method for forming a bioactive agent delivery composition comprising a bioactive agent-containing particulate, comprising steps of:
   forming a particle comprising a core particle comprising bioactive agent and a first biocompatible polymer, and a second biocompatible polymer comprising negatively charged groups, that is more water soluble first biocompatible polymer; and
   contacting the particle with a composition comprising cationic agent.

20. The method of claim 19 wherein the step of adding, the second biocompatible polymer comprises an acid group-containing biocompatible polymer, and the acid groups are partially or completely neutralized.

* * * * *